United States Patent
Moore et al.

(10) Patent No.: US 10,524,933 B2
(45) Date of Patent: Jan. 7, 2020

(54) VERSION PROTRACTOR

(71) Applicant: DEPUY (IRELAND), County Cork (IE)

(72) Inventors: Gary Moore, Wetherby (GB); Stephanie Prince, Wakefield (GB); Thomas P. Schmalzried, Rolling Hills, CA (US); Duncan Young, Hebden Bridge (GB)

(73) Assignee: DEPUY IRELAND UNLIMITED CO. (IE)

( * ) Notice: Subject to any disclaimer, the term of this patent is extended or adjusted under 35 U.S.C. 154(b) by 250 days.

(21) Appl. No.: 15/228,081

(22) Filed: Aug. 4, 2016

(65) Prior Publication Data
US 2018/0036143 A1 Feb. 8, 2018

(51) Int. Cl.
*A61F 2/46* (2006.01)

(52) U.S. Cl.
CPC .......... *A61F 2/4657* (2013.01); *A61F 2/4684* (2013.01); *A61F 2002/4668* (2013.01)

(58) Field of Classification Search
CPC ......... A61F 2/46; A61F 2/4657; A61F 2/4684
See application file for complete search history.

(56) References Cited

U.S. PATENT DOCUMENTS

| | | | |
|---|---|---|---|
| 3,229,372 A | 1/1966 | Quashnock | |
| 4,930,525 A | 6/1990 | Palestrant | |
| 5,188,121 A | 2/1993 | Hanson | |
| 5,196,019 A | 3/1993 | Davis | |
| 5,263,492 A | 11/1993 | Voyce | |
| 5,792,077 A | 8/1998 | Gomes | |
| 5,860,969 A * | 1/1999 | White | A61F 2/4657 623/23.35 |
| 6,120,510 A * | 9/2000 | Albrektsson | A61B 17/15 606/96 |
| 6,273,915 B1 | 8/2001 | Grimes | |
| 6,361,506 B1 * | 3/2002 | Saenger | A61B 5/1071 33/512 |
| 6,796,986 B2 | 9/2004 | Duffner | |
| 6,872,187 B1 | 3/2005 | Stark | |
| 7,018,383 B2 | 3/2006 | McGuire | |
| 7,559,931 B2 * | 7/2009 | Stone | A61B 34/20 606/91 |

(Continued)

FOREIGN PATENT DOCUMENTS

| | | |
|---|---|---|
| JP | 2014204768 A | 10/2014 |
| WO | WO 1998006359 A1 | 2/1998 |
| WO | WO 2005046475 A1 | 5/2005 |

*Primary Examiner* — Christopher J Beccia

(57) ABSTRACT

An apparatus and method for measuring a version angle of a restored neck of a femur during a hip replacement procedure. The apparatus includes a broach. The broach has a distal end that is insertable into a medullary canal of the neck of the femur. The broach also has a proximal end that extends along a neck axis of the broach. The apparatus also includes a protractor. The protractor includes a rod which is attachable to the proximal end of the broach to extend away from the neck axis of the broach for measuring the version angle of the restored neck of the femur relative to a vertical direction. The method includes inserting the broach, flexing the knee at approximately ninety degrees, orienting the tibia vertically, attaching the protractor to the proximal end of the broach and using it to measure the version angle.

12 Claims, 7 Drawing Sheets

(56) References Cited

U.S. PATENT DOCUMENTS

| | | |
|---|---|---|
| 7,571,548 B2 | 8/2009 | Taylor |
| 7,837,635 B2 | 11/2010 | Lissek |
| 2002/0165552 A1 | 11/2002 | Duffner |
| 2007/0266579 A1 | 11/2007 | Briscoe |
| 2010/0318191 A1 | 12/2010 | Branovacki |
| 2013/0053859 A1 | 2/2013 | Penenberg |
| 2013/0116699 A1* | 5/2013 | Smith ............... A61B 17/15 606/89 |

* cited by examiner

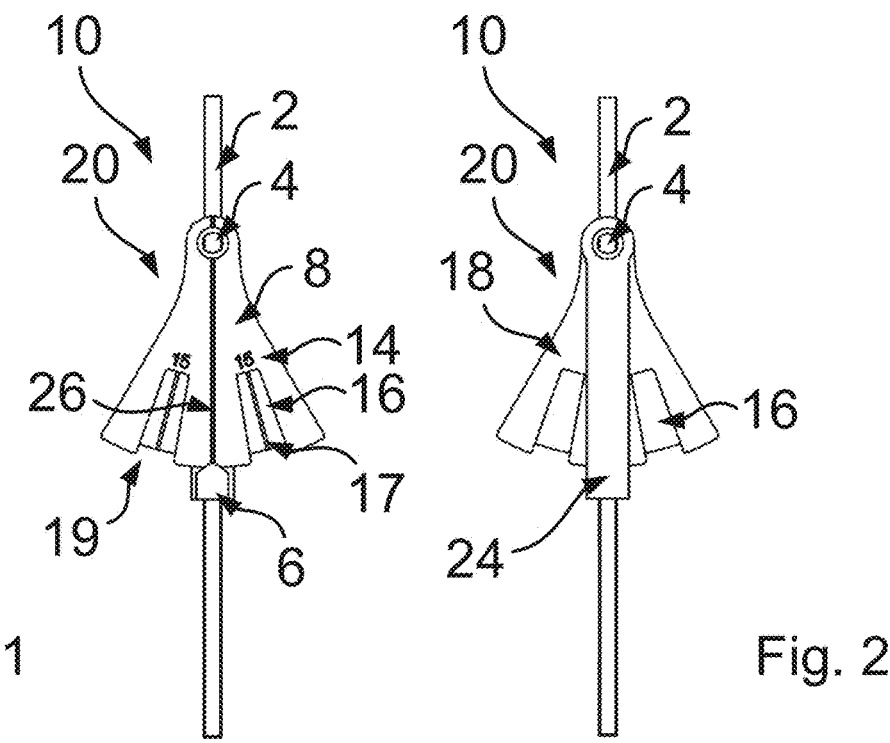
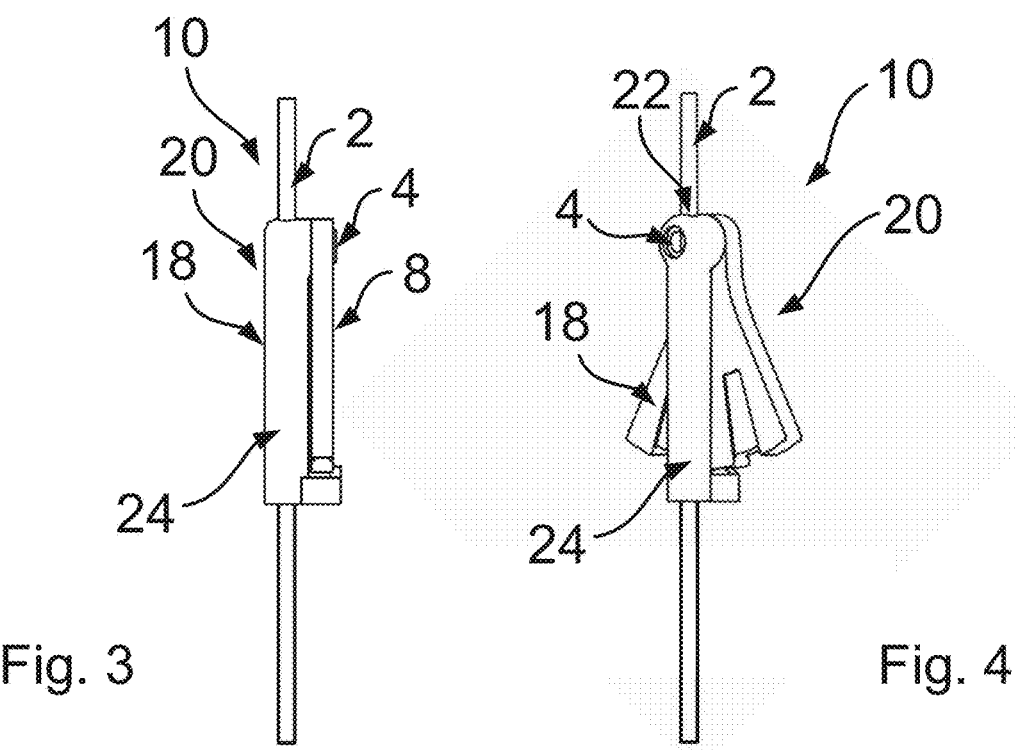

VERSION PROTRACTOR

BACKGROUND

The present specification relates to an apparatus for measuring a version angle of a restored neck of a femur during a hip replacement procedure, and to a method of measuring a version angle of a restored neck of a femur of a leg of a patient during a hip replacement procedure.

Hip replacement is a surgical procedure in which the hip joint is replaced by a prosthetic implant. As part of the hip replacement procedure, the femoral head is replaced with a femoral prosthetic that includes a stem which is inserted into the medullary canal at the neck of the femur. The femoral prosthetic also includes a bearing surface, which is received within the acetabulum of the patient. The procedure may in some cases also involve inserting an acetabular cup into the acetabulum of the patient, for receiving the bearing surface of the femoral prosthetic.

It is important that the size, shape, orientation and alignment of the femoral prosthetic and the acetabulum (or acetabular cup, where one is used) are determined correctly, to ensure correct operation of the hip joint. For instance, misalignment between the femoral prosthetic and the acetabulum (or acetabular cup, where one is used) may lead to complications such as increased wear and tear of the bearing surfaces and/or unbalanced tension in the surrounding ligaments.

As part of this, it is important that the version angle of the restored neck of the femur is determined correctly for the patient in question. A typical version angle for many patients is around 15 degrees of anteversion, however this can vary between patients.

SUMMARY

Aspects of the present invention are set out in the accompanying independent and dependent claims. Combinations of features from the dependent claims may be combined with features of the independent claims as appropriate and not merely as explicitly set out in the claims.

According to an aspect of the invention, there is provided an apparatus for measuring a version angle of a restored neck of a femur during a hip replacement procedure, the apparatus comprising:

a broach comprising a distal end insertable into a medullary canal of the neck of the femur and a proximal end extending along a neck axis of the broach; and a protractor comprising a rod which is attachable to the proximal end of the broach to extend away from the neck axis of the broach for measuring the version angle of the restored neck of the femur relative to a vertical direction.

According to another aspect of the invention, there is provided a method of measuring a version angle of a restored neck of a femur of a leg of a patient during a hip replacement procedure, the method comprising:

inserting a distal end of a broach into a medullary canal of the neck of the femur;

flexing a knee of the patient at approximately ninety degrees;

rotating the leg of the patent to orient a tibia of the leg along a vertical direction;

attaching a protractor comprising a rod to a proximal end of the broach to extend away from the neck axis of the broach; and using the protractor to measure the version angle of the restored neck of the femur relative to the vertical direction.

Embodiments of this invention may conveniently allow a version angle of a restored neck of a femur of a leg of a patient to be measured during a hip replacement procedure. This can allow misalignment to be avoided between a femoral prosthesis located in the restored neck and the acetabulum of the patient (or acetabular cup, where one is used), which receives a bearing surface of the femoral prosthesis. In the event that the measured version angle differs from an intended or "normal" angle, measures may be taken to accommodate for this, such as adjusting the alignment of the acetabular cup or choosing a different femoral implant for the replacement hip.

The protractor may include a pendulum pivotably mounted on the rod to hang vertically for measuring the version angle relative to the vertical direction. The method may include allowing the pendulum to hang vertically, for measuring the version angle relative to the vertical direction. Accordingly, with the tibia held vertically, gravity may conveniently be used to define the vertical direction relative to which the version angle is measured.

A stationary marker may be attached to the rod for reading off a measurement of the version angle relative to the vertical direction. The method may further include reading off a measurement of the version angle relative to the vertical direction by determining the location of the stationary marker in relation to the orientation of the pendulum.

In some embodiments, the protractor may include a sleeve portion located on the rod. The sleeve portion may include the stationary marker. The pendulum may be pivotably attached to the sleeve portion.

In one embodiment, the protractor may include a bubble level attached to the rod. The method may further include using the bubble level to read off the version angle relative to the vertical direction.

In some examples, the protractor may include one or more indicia for reading off a measurement of the version angle relative to the vertical direction. The method may further include reading off a measurement of the version angle relative to the vertical direction using the indicia. In some examples the indicia may include a plurality of tick marks for reading off a numerical measurement of the version angle in degrees. The method may further include reading off a numerical measurement of the version angle in degrees using the tick marks. In some examples, the indicia may include one or more zonal markers. The zonal markers may each correspond to a range of version angles. For instance, the range may be a normal range, a high range (within which the version angle is higher than normal) and/or a low range (within which the version angle is lower than normal). The method may further include reading off a zonal measurement indicating that the version angle falls within either a normal range, a high range and/or a low range using the zonal marker(s). In some examples, the indicia may further include a marker for indicating the vertical direction. The marker may, for instance be a line extending across the pendulum, such that the line is vertically oriented when the pendulum is allowed to hang vertically.

In some embodiments, the protractor may include an electronic inclinometer attached to the rod. The method may further include using the electronic inclinometer to read off the version angle.

In one embodiment, the rod may include an elongate section set at a predetermined angle relative to the broach. The predetermined angle may correspond to a normal version angle for a patient (e.g. 15 degrees). The method may further include measuring the version angle by judging (e.g.

simply by line of sight) the orientation of the elongate section relative to the vertical direction.

In one embodiment, the proximal end of the broach may include a connection member for connecting a neck trial to the broach. The apparatus may further include a neck trial attached to the connection member of the broach. Attaching the protractor to the proximal end of the broach may include attaching the rod to the connection member or to the neck trial.

In some embodiments, the proximal end of the broach (e.g. the connection member and/or the neck trial) may include an aperture for receiving the rod. Attaching the protractor to the proximal end of the broach may include inserting the rod in the aperture.

BRIEF DESCRIPTION OF THE DRAWINGS

Embodiments of this invention will be described hereinafter, by way of example only, with reference to the accompanying drawings in which like reference signs relate to like elements and in which:

FIGS. 1 to 4 show various views of a protractor according to an embodiment of this invention;

DETAILED DESCRIPTION

Figure 5:
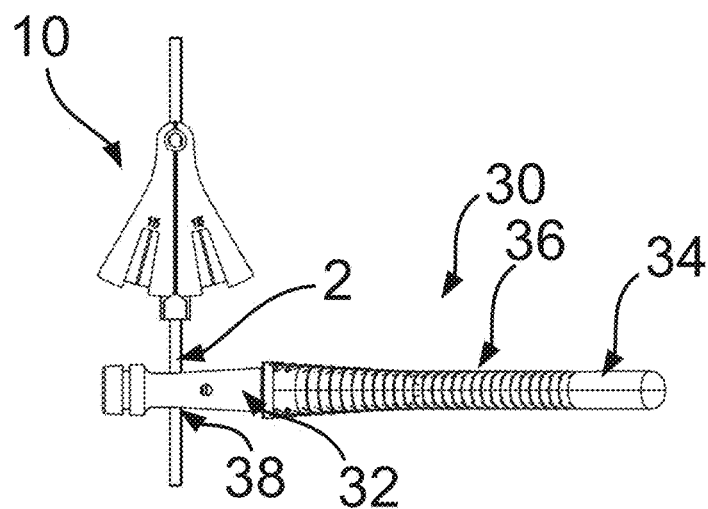
FIGS. 5 to 7 show various views of the protractor of FIGS. 1 to 4 assembled together with a broach having a neck trial, according to an embodiment of this invention.

Embodiments of this invention are described in the following with reference to the accompanying drawings.

FIGS. 1 to 4 show various views of a protractor according to an embodiment of this invention. The protractor 10 in this example includes a rod 2 which, as described below is attachable to the proximal end of a broach for use in measuring a version angle of a restored neck of a femur during a hip replacement procedure. The rod is elongate and may, for instance, be circular in cross section.

The protractor 10 in this example includes a pendulum 20, which is pivotably mounted on the rod 2. As will be described below, the pendulum 20 may be arranged to hang vertically from the rod 2 for measuring the version angle relative to the vertical direction.

The protractor 10 may include a sleeve 24, which may also be elongate. The sleeve 24 includes a bore 22, through which the rod 2 may be received, thereby to attach the sleeve 24 to the rod 2. The bore 22 may be sized so as to provide a firm friction fit between the sleeve 24 and the rod 2. The fit between the sleeve 24 and the rod 2 may be tight enough to hold the sleeve 24 in a fixed position relative to the rod 2. The fit between the sleeve 24 and the rod 2 may still be loose enough to allow the surgeon manually to adjust the location and orientation of the sleeve 24 relative to the rod 2 (e.g. the rotational position of the sleeve 24 around the longitudinal axis of the rod 2 and/or the position of the sleeve 24 along the length of the rod 2).

In this example, the pendulum 20 is attached to the sleeve 24 by a pivot 4, which may be located at or near to the top of the pendulum 20. The pivotal attachment of the pendulum 20 to the sleeve 24 in this example implements the pivotal mounting of the pendulum 20 on the rod 2 noted above.

The pendulum 20 may include a front face 8 and a rear face 18. The pendulum 20 may be provided with one or more indicia for reading off a measurement of the version angle relative to the vertical direction. These indicia may be provided on the front face 8 and/or the rear face 18 of the pendulum 20.

The protractor 10 may also include a stationary marker 6. In the present example, the stationary marker 6 is located on the sleeve 24. The stationary marker may, for instance, be a needle or arrow pointing towards a lower edge 19 of the pendulum 20. As the pendulum 20 rotates around the pivot 4 (under the force of gravity, thereby to hang vertically) the indicia move relative to the stationary marker 6, allowing the version angle to be read off from the protractor 10 by noting the position of the stationary marker 6 relative to the indicia at the lower edge 19 of the pendulum 20.

In the present example, the indicia include a pair of zonal markers 16 for reading off a zonal measurement indicating that the version angle falls within either a normal range, a high range and/or a low range. Each zonal marker 16 may, for instance comprise an area on the front face 8 (and/or rear face 18) of the pendulum 20 which indicates a range of angles (e.g. a 5 degree or 10 degree band). Each zonal marker may, for instance, be coloured differently to the surrounding area of the pendulum to allow to be viewed easily.

The zonal markers 16 may be provided with one or more tick marks 17, for indicating e.g. a mid-point of the zone covered each the zonal marker 16. In the example shown in FIGS. 1 to 4, two zonal markers 16 are included on the front face 8 of the pendulum 20, with each zonal marker being centred around a 15 degree angle of rotation of the pendulum 20 relative to the rod 2. The angle of 15 degrees is chosen in this example since this is often considered to be the "normal" version angle for a patient. It is envisaged that angle other than 15 degrees may be chosen. The zone covered by each zonal marker 16 may be chosen to provide an acceptable amount of tolerance either side of the "normal" version angle (e.g. ±2.5 degrees, or ±5.0 degrees), within which it may be determined that the version angle provided by the restored neck of a femur is acceptable.

One or more numerical indications 14 of the angle(s) covered by each zonal marker 16 may be provided on the front face 8 of the pendulum 20. In the present example, the numerical indication 14 specifies the central angle of 15 degrees around which each zonal marker 16 is centred. Similar numerical indication may also be provided at the edges of each zonal marker 16.

Note that the zonal markers 16 may be arranged symmetrically on either side of the front face 8 of the pendulum 20, so that one of the zonal markers 16 may be used for carrying out a procedure on the left leg of a patient while the other of the zonal markers 16 may be used for carrying out a procedure on the right leg of a patient.

In the present example, the pendulum 20 is substantially triangular, with an upper apex of the triangle being located at or near the pivot 4. The lower edge 19 of the triangle, which may correspond to a side of the triangle opposite the upper apex including thee pivot 4 may be curved (convex), so that the distance between the lower edge 19 and the stationary marker 6 remains substantially unchanged as the pendulum 20 rotates around the pivot 4. In the present example, the zonal markers are recessed slightly with respect to the lower edge 19 of the pendulum 20, so as to emphasise their position relative to the stationary marker 6.

Instead of (or as well as) the zonal markers 16 described above, it is envisaged that the indicia may include a plurality of tick marks for reading off a numerical measurement of the version angle in degrees or radians. These tick marks may be located at the bottom edge 19 of the pendulum to allow the angle to be conveniently read off using the stationary marker 6. The tick marks may be spaced at regular intervals (e.g. every 1, 2, or 5 degrees). The tick marks may be provided with numerical indications of the angle associated with each tick mark.

In some embodiments, the pendulum 20 may be provided with a further marker 26 for indicating the vertical direction when the pendulum 20 hangs vertically under the force of gravity. The further marker 26 may for instance include a line which extends along the front face 8 of the pendulum 20. In the example of FIGS. 1 to 4, the further marker 26 extends along the front face 8, in between the zonal markers 16. The further marker 26 may also pass through the pivot 4, as shown in FIG. 1. As will be described below, the further marker 26 may be used by a surgeon to determine the vertical direction when using the protractor 10, for instance to check whether the tibia of the patient is oriented vertically while he or she is reading off the version angle.

The rod 2 may, for instance, comprise Precipitation Hardened Stainless Steel e.g. 17-4PH Grade of Stainless Steel. The pendulum 20 and sleeve 24 may comprise engineering plastic such as Polyphenylsulphone (PPS), commonly known by the brand "Radel" from Solvay Chemicals, Modified PolyArylEtherKetone/PolyEtherEtherKetone (mPEEK), commonly known by the brand "Avaspire" from Solvay Chemicals or PolyAcetal/PolyOxyMethylene (POM), Commonly known as "Acetal" or by the brand name "Celcon". There are other options—Propylux, Nylon 66, or other polymers that may normally be used for single-use applications. The sleeve 24 may alternatively be made from Stainless Steel 17-4PH.

Figure 6:
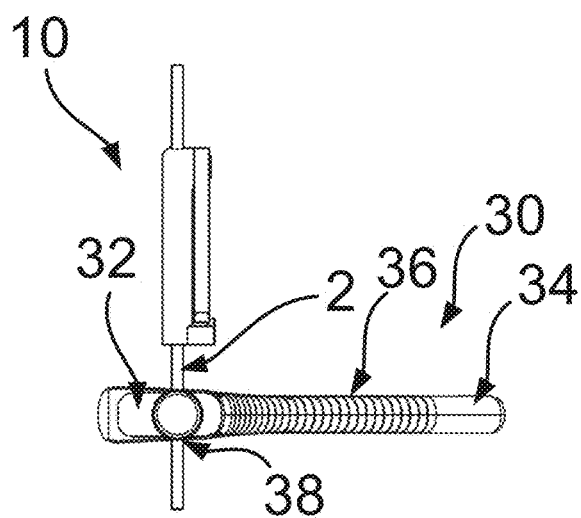
Figure 7:
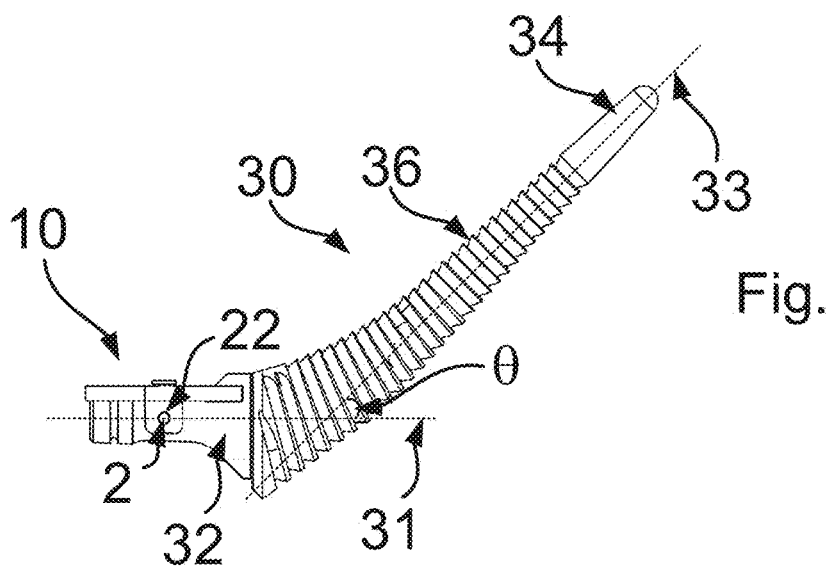

FIGS. 5 to 7 show various views of the protractor 10 of FIGS. 1 to 4 assembled together with a broach 30 according to an embodiment of this invention.

The broach 30 in this example is a trial femoral broach which is sized and shaped to be received in the medullary canal of the neck of the femur during a hip replacement procedure. In particular, the broach 30 has a distal end including a cutting portion 36 and a tip 34, both of which may be inserted into the medullary canal, and a proximal end including a trial neck portion 32. The cutting portion 36 may include a surface comprising a plurality of teeth which may, as is known in the art, be used to remove bone from the femur during a hip replacement procedure, thereby to prepare the femur to receive the stem of a femoral prosthetic. The distal end of the broach 30 may extend along a longitudinal axis thereof, which is labelled using reference numeral 33 in FIG. 7. The broach 30 may, for instance, comprise Precipitation Hardened Stainless Steel e.g. 17-4PH Grade of Stainless Steel, 404 Grade of Stainless Steel, 300 series (e.g. 316 or 303 stainless steel), Nitronic 60 Stainless Steel, Cobalt-Chrome alloy, Titanium alloy, Fibre-reinforced PEEK polymer, PEEK polymer or a ceramic material such as alumina [aluminum oxide] and zirconia [zirconium oxide].

The trial neck extends along a neck axis 31 of the broach 30. The neck axis 31 is typically set at an angle (denoted "θ" in FIG. 7) to the longitudinal axis 33 of the distal end. The trial neck portion 32 may be removably attached to a connection member of the broach (this will be described below in more detail in relation to FIG. 15). This may allow trial neck portions of different sizes and lengths to be used with the broach 30, according to the chosen dimensions of the femoral implant. It is also envisaged that the trial neck portion 32 may be integrally formed with the distal end of the broach 30.

The distal end of the broach 30 may be dimensioned similarly to the stem of the femoral implant, and the trial neck portion 32 may be dimensioned and oriented similarly to the neck of the femoral implant, so that the broach 30 may also be used as a trial during the procedure, the determine the position and orientation of the femoral implant once it has been installed. Note that the angle at which the neck axis 31 of the broach 31 is set relative to the distal end of the broach 30 may correspond to the angle of the neck axis of the femoral implant relative to the stem of the femoral component.

To use the broach 30 as a trial, the surgeon may, as part of the procedure for removing bone from the femur to prepare it to receive the femoral implant, periodically insert the distal end of the broach 30 into the femur to judge the fit of the implant in the prepared femur. As part of this, the protractor 10 described above may be attached to the proximal end of the broach 30 as indicated in FIGS. 5-7 to allow the surgeon to measure the anticipated version angle of the restored neck of a femur, once the femoral implanted has been installed. This can allow the surgeon to check that the version angle for the restored neck of the femur will be correct (e.g. within a certain tolerance) for the patient. The process for measuring the version angle using the protractor 10 and broach 30 will be described in more detail below in relation to FIGS. 11-13.

As can be seen in FIGS. 5-7, the neck trial 32 of the broach 30 is configured to allow the protractor 10 to be attached to it so that the rod 2 extends away from the proximal end of the broach 30. In FIG. 7 it is shown that, in the present embodiment, when the protractor 10 is attached to the neck trial 32, the longitudinal axis of the rod 2 is oriented substantially orthogonal to the neck axis 31. The rod 2 may also be oriented so that it extends substantially perpendicular the plane containing the neck axis 31 and the longitudinal axis 33 of the distal end of the broach 30.

To allow attachment of the protractor 10 to the neck trial 32, the neck trial 32 in this example is provided with an aperture 38 through which the rod 2 of the protractor 10 may be received. The aperture 38 passes through the neck trial 32 from a posterior face to an anterior face thereof, and may optionally also pass through a point on the neck axis 31 as can be seen in FIG. 7. Note that when the protractor 10 is attached to the neck trial 32 in this example, the longitudinal axes of the rod 2, the bore 22 and the aperture 38 are all aligned with each other. The aperture 38 may be sized so as to provide a firm friction fit between the aperture 38 and the rod 2. The fit between the aperture 38 and the rod 2 may be tight enough to hold the rod 2 in a fixed position relative to the neck trial 32. The fit between the aperture 38 and the rod 2 may still be loose enough to allow the surgeon manually to adjust the location and rotational orientation of the rod 2 relative to the neck trial 32.

When the broach 30 is inserted into the medullary canal of the femur, the plane containing the axes 31 and 33 is tilted by a certain an amount, according to the version angle of the restored neck of the femur. This tilting of the broach 30 also causes the rod 2 to tilt, while the pendulum 20 of the protractor 10 rotates around the pivot 4 to maintain its vertical orientation. As will be described below this can, by correct orientation of the leg by the surgeon so that the tibia points along the vertical direction, allow the protractor 10 to be used to measure the version angle of the restored neck of the femur.

Figure 8:
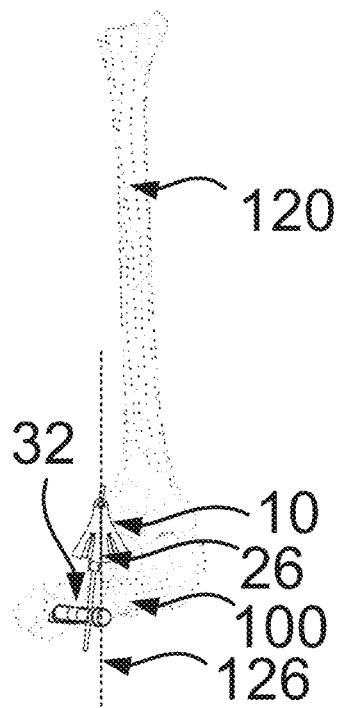
FIGS. 8 to 10 show various views of the protractor and broach of FIGS. 5 to 7 in situ during part of a hip replacement procedure according to an embodiment of this invention.
Figure 9:
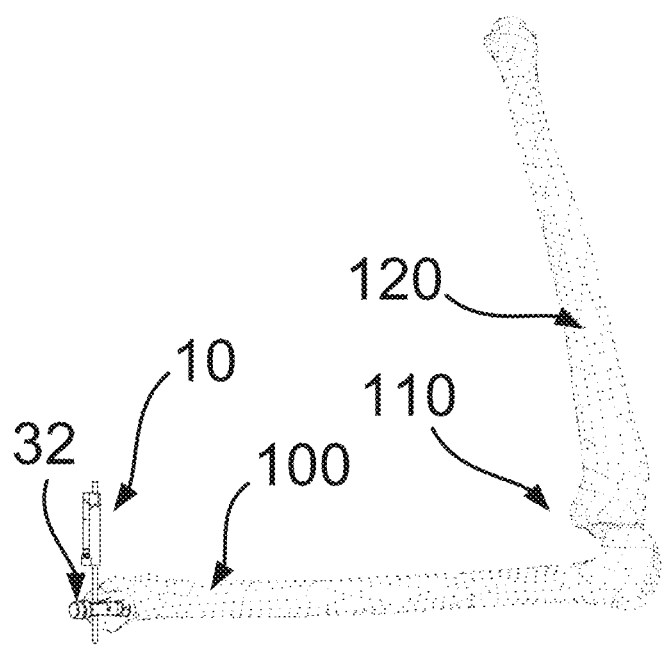
Figure 10:
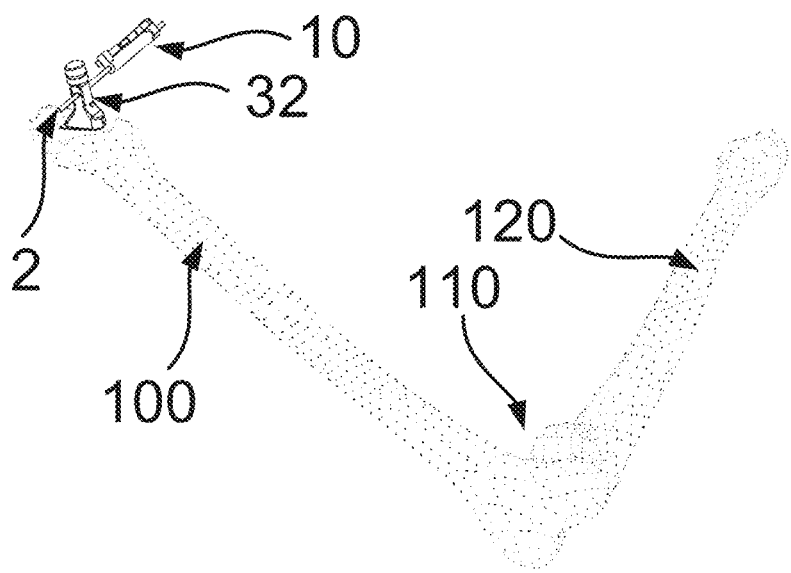

FIGS. 8 to 10 show various views of the protractor 10 and broach 30 of FIGS. 5 to 7 in situ during part of a hip replacement procedure according to an embodiment of this invention. As part of a hip replacement procedure, the distal end of the broach 30 is inserted within the medullary canal of the neck of the femur 100. The knee joint 110 and tibia 120 of the leg are also shown in FIGS. 8-10. The procedure also includes (either before or after the broach 30 has been inserted) flexing the knee 110 of the patient at approximately ninety degrees and rotating the leg of the patent to orient a tibia 120 along the vertical direction. Note that it is envisaged that in some examples, the leg would be rotated first, prior to flexing the knee 110 of the patient at approximately ninety degrees. This manipulation of the leg and the use of the protractor 10 for measuring the version angle of the restored neck of the femur may be included as part of a hip replacement procedure following the so called "posterior approach", although in principle it may also be included in a hip replacement procedure following other approaches such as the anterior approach, the lateral approach, direct lateral approach, direct anterior approach, or postero-lateral approach.

As can be seen in FIGS. 8 to 10, as part of the procedure, the protractor 10 is attached to the broach 30, so that the pendulum 20 (and sleeve 24) of the protractor 10 is located posteriorly with respect to the broach 30. Typically, the protractor 10 may be attached to the broach 30 after once the leg has been manipulated to so point the tibia 120 along the vertical direction as described above, although it is also envisaged that the protractor 10 could instead be attached prior to the manipulation of the leg. With the pendulum 20 of the protractor 10 located posteriorly with respect to the broach 30, the pendulum 20 hangs vertically. As can be seen in FIG. 8, the further marker 26 is aligned parallel with the vertical direction, which is represented in FIG. 8 by the dotted line 126.

In this position, with the tibia oriented vertically, the version angle of the restored neck of the femur 100 causes the broach 30 and consequently the rod 2 of the protractor to tilt. The amount of tilting corresponds to the version angle of the version angle of the restored neck of the femur 100, which may read off from the protractor 10 using the stationary marker 6. Some examples of this are shown in FIGS. 11 to 13.

Figure 11:
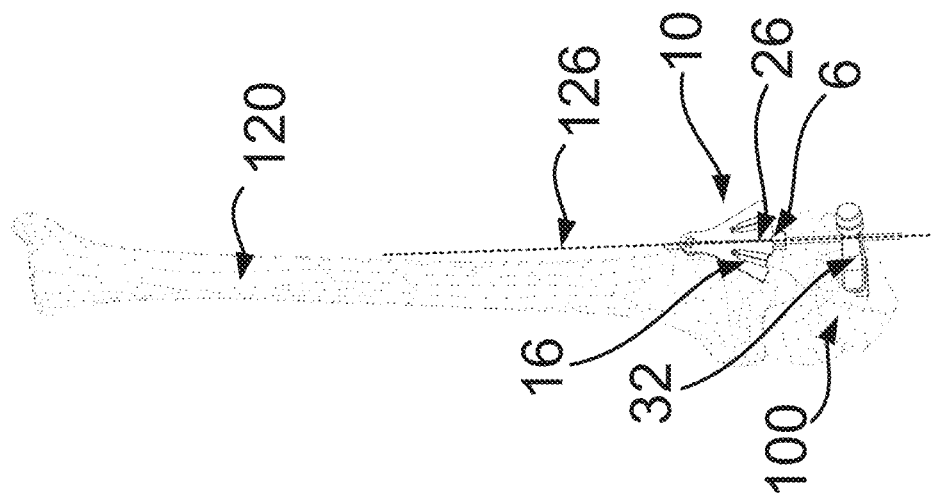
FIGS. 11 to 13 illustrate the measurement of a version angle according to an embodiment of this invention.
Figure 12:
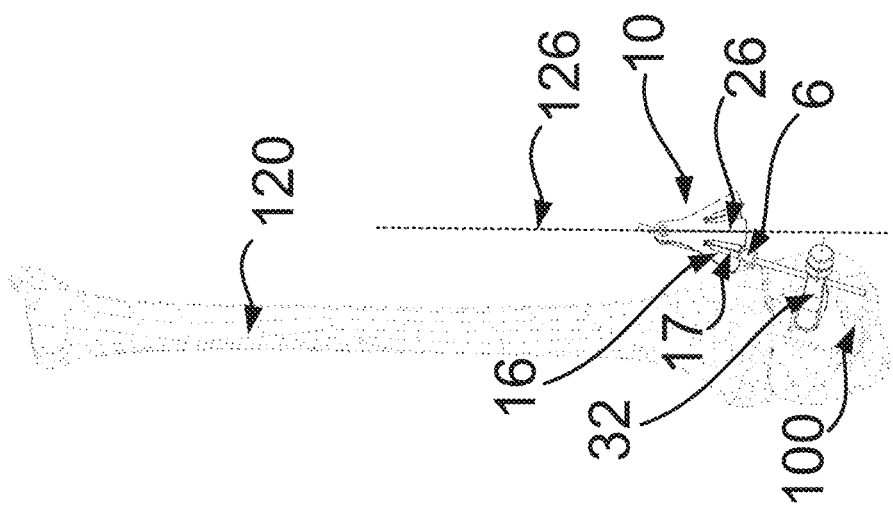
Figure 13:
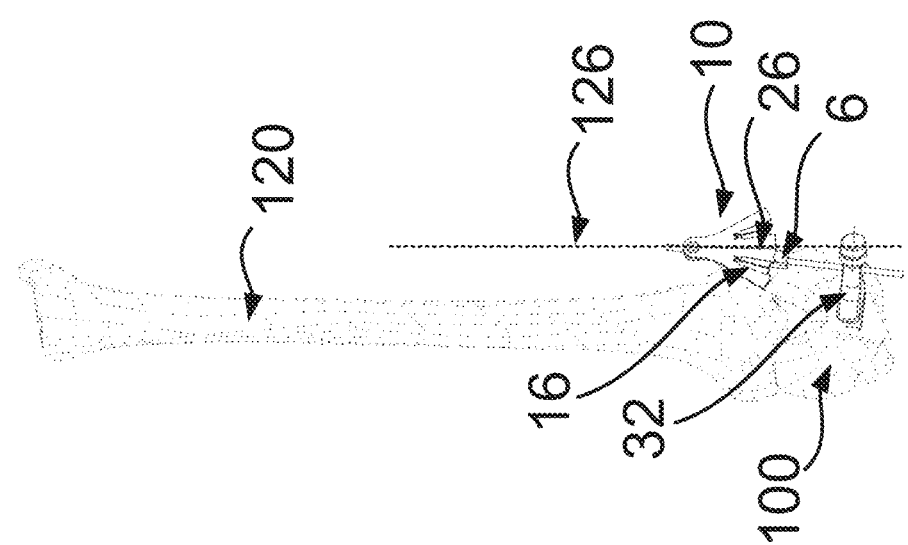

The view of the leg, broach 30 and protractor 10 in FIGS. 11-13 is along the femoral axis, looking down towards the knee 110 from the neck of the femur 100. Note that the tibia 120 is oriented vertically as discussed above. The broach 30 is inserted into the medullary canal at the restored neck of the femur 100 and the protractor 10 is attached to the broach 30 so that the pendulum 20 is located posteriorly with respect to the femur 100 and the broach 30. As the pendulum 20 of the protractor 10 hangs along the vertical direction 126, the surgeon may compare the position of the stationary marker 6 with respect to the indicia on the pendulum, thereby to measure the version angle. In the examples shown in FIGS. 11 to 13, the indicia include a pair of zonal markers of the kind discussed above, although again it is envisaged that other kinds of indicia, such as tick marks may be provided on the protractor 10.

In FIG. 11, the position of the stationary marker 6 relative to the zonal marker 16 indicates that the version angle falls outside the acceptable range indicated by the zonal marker 16. In particular, FIG. 11 shows an example in which the version angle of the restored neck of the femur is non-zero, but is too low. The broach 30 in FIG. 11 is thus retroverted relative to the amount of anteversion that would normally be considered to be within the normal range.

On the other hand, FIG. 12 shows an example in which the version angle of the restored neck of the femur falls within the acceptable range covered by the zonal marker 16. This indicates that the broach 30 is anteverted by an amounted that would be considered normal. In fact, in the example of FIG. 12, the version angle is approximately 15 degrees (which, as discussed above, may be considered to be roughly average for a human leg), which can be determined from the fact that the stationary marker 6 is substantially aligned with the central tick mark 17.

FIG. 13 shows an example in which the version angle of the restored neck of the femur is even lower than that of the example of FIG. 11. In FIG. 13, the broach 30 is thus significantly retroverted relative to the amount of anteversion that would normally be considered to be within the normal range (note that the stationary marker 6 in FIG. 13 is located slightly to the right of the further marker 26, instead of to the left of the further marker 26 as shown in the examples of FIGS. 11 and 12).

Figure 14:
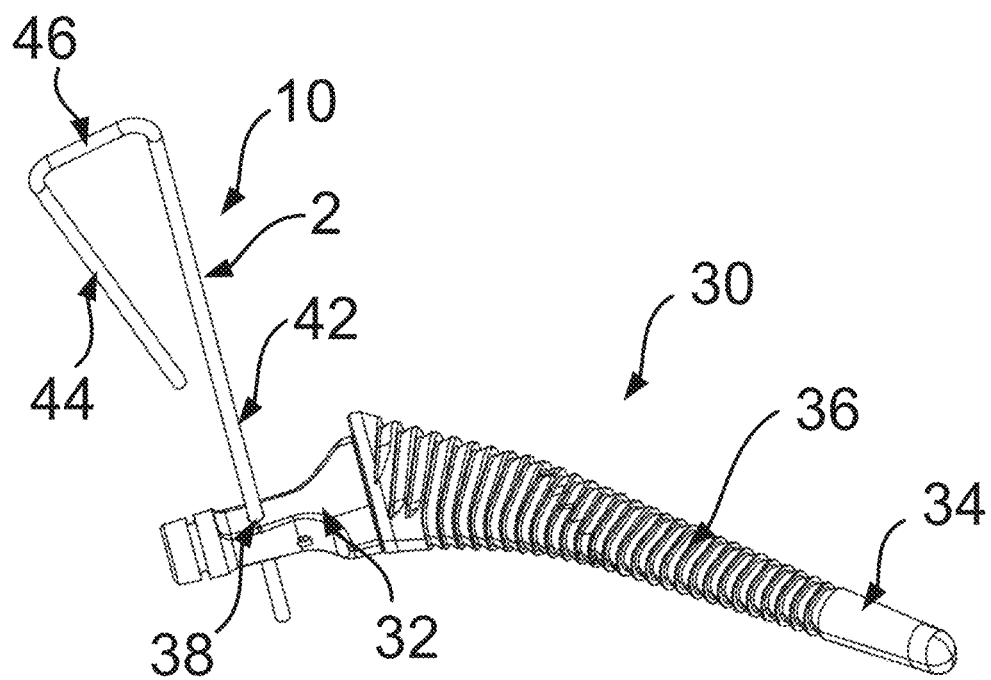
FIG. 14 shows a protractor assembled together with a broach having a neck trial, according to an embodiment of this invention.

FIG. 14 shows another example of an apparatus for measuring a version angle of a restored neck of a femur during a hip replacement procedure. As described previously, the apparatus includes a broach 30. The broach 30 in this example is substantially the same as that described above in relation to FIGS. 5-7.

The apparatus in FIG. 14 also includes a protractor 10. In this embodiment, the protractor includes a rod 2, which includes a first section 42, a second section 46 and a third section 44. The third section 44 is elongate, the first 42 and second 44 sections may also be elongate. As described previously, the protractor 10 may be attached to the broach 30 by inserting the rod 2 into the aperture 38 of the neck trial 32 of the broach 30. In this example, the rod 2 is bent in two places so as to produce the first 42, second 46 and third 44 sections, with the third section 44 set at a predetermined angle relative to the broach 30 when the rod 2 is attached to the broach 30. It is envisaged that the rod may include further sections and bends.

Figure 16:
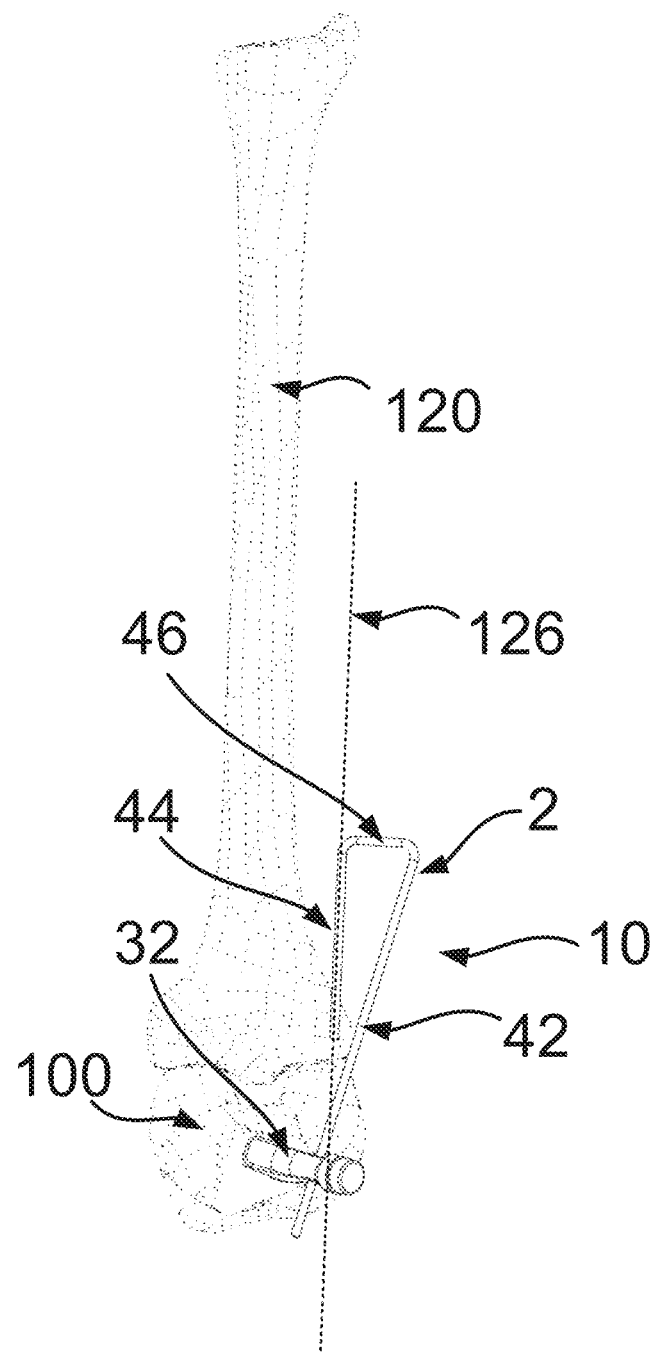
FIG. 16 illustrates the measurement of a version angle according to an embodiment of this invention, and FIG. 17 show a protractor according to a further embodiment of this invention.

The predetermined angle at which the third section 44 is set relative to the broach 30 may correspond to a normal version angle for a patient, for example 15 degrees. FIG. 16 shows the use of the broach 30 and attached protractor 10 of FIG. 14 for measuring the version angle of the restored femoral neck of the femur. As with FIGS. 11 to 13, the view of the leg, broach 30 and protractor 10 in FIG. 16 is along the femoral axis, looking down towards the knee 110 from the neck of the femur 100. Again, note that the tibia 120 is oriented vertically by rotation of the leg and flexing of the knee as discussed above. The broach 30 is inserted into the medullary canal at the restored neck of the femur 100 and the protractor 10 is attached to the broach 30 so that the third section 44, which is elongate, is located posteriorly with respect to the femur 100 and the broach 30.

With the broach 30 and protractor 10 in place as shown in FIG. 16, and with the tibia 120 oriented vertically, the surgeon may inspect the third section 44 to judge its orientation relative to the vertical direction. In this way, he or she may measure the version angle of the restored neck of the femur 100. For instance, in the example shown in FIG. 16, the tilting of the broach 30 and the consequent tilting of the protractor 30 according to the version angle of the restored neck of the femur as explained previously orients the third section 44 of the protractor 10 such that it is substantially parallel to the vertical direction 126. Since the angle at which the third section is set with respect to the broach 30 in this example is approximately 15 degrees, this orientation of the third section 44 allows the surgeon to determine that the version angle is normal. On the other hand, should the surgeon observe that the third section 44 is not oriented vertically, this would allow him or her to determine that the version angle differs from the predetermined angle of the third section 44.

The surgeon may also judge, by comparing the orientation of the third section 44 with respect to the vertical direction, whether the version angle of the restored femoral neck of the femur falls within an acceptable range. In some examples, a surgical kit may include a plurality of protractors 10 of the kind shown in FIG. 14, each protractor 10 having a third section 44 which is set at a different predetermined angle. In this way the surgeon may be able to swap between different protractors 10 until the third section 44 of the chosen protractor 10 aligns vertically when the tibia 120 is aligned vertically. The surgeon may then determine the version angle according to the predetermined angle of the third section 44 of the chosen protractor 10.

In the examples described above, the protractor 10 is attached to the broach by inserting the rod 2 into an aperture 38 that passes through the neck trial 32 of the broach 30, from an anterior face of the neck trial 32 to a posterior face of the neck trial 32. It is envisaged that the apparatus described herein may include a broach 30 having a detachable neck trial 32, to allow differently configured neck trials 32 to be used (e.g. neck trials 32 of different sizes and/or having a different version angle). A surgical kit according to an embodiment of this invention may include one or more such broaches 30 (e.g. of different sizes) and one or more such neck trials 32 for attachment to each broach 30.

Figure 15:
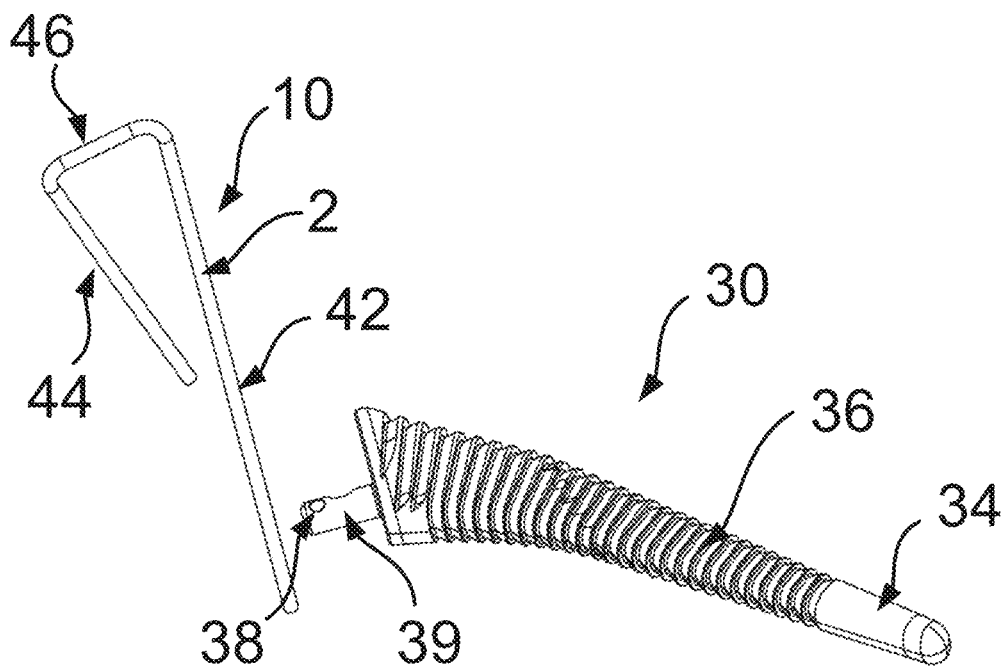
FIG. 15 shows a protractor and broach according to an embodiment of this invention.

To implement this, the proximal end of the broach 30 may be provided with a connection member 39 of the kind shown in FIG. 15. The neck trials 32 used with a broach 30 of the kind shown in FIG. 15 may include a corresponding (female) connector for receiving the connection member 39, thereby to allow the neck trials 32 to be attached at the proximal end of the broach 30.

As shown in FIG. 15, instead of attaching the protractor 10 to the neck trial 32 of the a broach 30 as described previously, it is envisaged that the protractor 10 may instead be attachable to the connection member 39 at the proximal end of the broach 30. For instance, in FIG. 15, an aperture 38 is located in the connection member 39, which passes through the connection member 39 from an anterior side to a posterior side thereof, for receiving the rod 2 of the protractor 10. It is envisaged the a connection member configured in this way may allow any of the protractors 30 described herein to be attached to the broach 30, although in FIG. 15 a protractor 10 of the kind shown in FIGS. 14 and 16 is provided.

Figure 17:
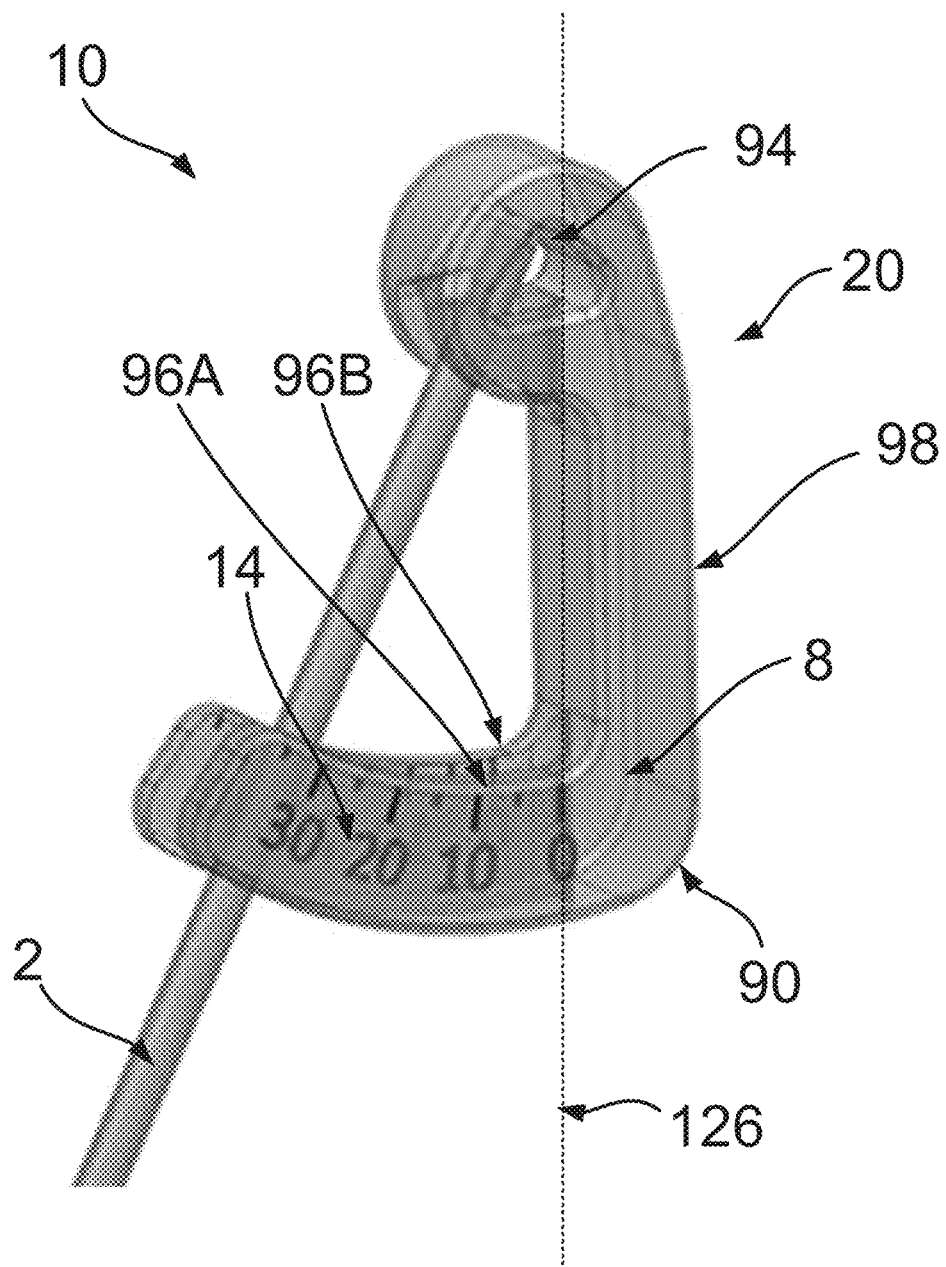

FIG. 17 show a protractor 20 according to a further embodiment of this invention. In common with the previously described embodiments, the protractor 10 in this example includes a rod 2 which, as described below is attachable to the proximal end of a broach for use in measuring a version angle of a restored neck of a femur during a hip replacement procedure. The rod 2 is elongate and may, for instance, be circular in cross section.

The protractor 10 in this example includes a pendulum 20, which is pivotably mounted on the rod 2. The pendulum 20 may include an arm 98 having an elbow 90 and an angled member 96 set at an angle (e.g. around 90 degrees) to the arm 98. The arm 98 may include (e.g. at a top end thereof) a pivot point 94 which can rest upon an end of the rod 2 distal the broach with which the protractor 10 is used, so that the pendulum 20 can rotate freely about the point 94 under its own weight. To facilitate free hanging of the pendulum 20 under gravity, the end of the rod 2 may be rounded (e.g. hemispherical). Correspondingly, the pivot point 94 may for instance be formed from a curved (e.g. hemispherical) socket, which receives the end of the rod 2. Accordingly, in common with the embodiment of FIGS. 1 to 13, the pendulum 20 may be arranged to hang vertically from the rod 2 for measuring the version angle relative to the vertical direction. In the present embodiment, as the pendulum 20 hangs vertically under its own weight, the arm 98 may extend substantially along the vertical direction 126.

The angled member 96 may be bifurcated into two parts 96A, 96B. In use a space or slot located in between the two parts 96A, 96B may receive the rod 2, thereby allowing the pendulum 20 to rotate freely relative to the rod 2 while preventing movement of the pendulum 20 outside the plane containing the rod 2 and the vertical direction 126.

As can be seen in FIG. 17, the pendulum 20 may be provided with indicia for reading off a measurement of the version angle relative to the vertical direction. The indicia may be provided on a front face 8 of the pendulum and/or on a rear face of the pendulum 20. In the present example, the indicia include numerical indications 14 of angle relative to the vertical direction (note that the "0" point shown in FIG. 17 coincides with the vertical direction) and a plurality of corresponding tick marks. To read off the version angle, the surgeon may note the position of the rod 2 relative to the angled member 96 using the tick marks and numerical indications 14. It is envisaged that in other examples, zonal markers of the kind described above may be provided on the front face 8 and/or rear face of the pendulum 20 (e.g. on the angled member 96) for measuring the version angle.

The protractor 10 shown in FIG. 17 may be used in much the same way as the protractor described in relation to FIGS. 1 to 13 for measuring the version angle, by attaching the rod to the proximal end of a broach to and allowing the pendulum 20 to hang vertically.

In accordance with an embodiment of the invention, a protractor may include alternative means for measuring the version angle.

For instance, in one embodiment, the protractor may include a bubble level which may be attached to the proximal end of the broach. The bubble level may be located on a rod of the kind described above, which again may be inserted into an aperture located either in the neck trial or connection member (e.g. so that the bubble level is located posteriorly with respect to the femur and broach). The bubble level may be curved (e.g. substantially C-shaped), so that the location of the bubble can be used to read off the particular angle at which the bubble level is oriented relative to the vertical direction. As explained previously, this angle would correspond to the version angle of the restored neck of the femur during. The bubble level may be provided with indicia of the kind described above, including zonal markers and/or one or more tick marks positioned to allow the position of the bubble in the bubble level to be used to read off the version angle and/or determine whether the version angle falls within an acceptable range.

In another example, the protractor may include an electronic inclinometer which may be attached to the proximal end of the broach. The electronic inclinometer may be located on a rod of the kind described above, which again may be inserted into an aperture located either in the neck trial or connection member (e.g. so that the electronic inclinometer is located posteriorly with respect to the femur and broach). The electronic inclinometer may be configured to measure its orientation relative to the vertical direction, thereby to measure the tilting of the broach according to the version angle of the restored neck of the femur as explained previously. The electronic inclinometer may include a display for displaying the measured angle and/or indicating whether the version angle falls within an acceptable range. In some examples, instead of, or in addition to including a display, the electronic inclinometer may be configured to send the measured angle via a wired or wireless connection to a separate computing device for display and/or use in making recommendations on a pre-operative plan and the desired outcome for the patient.

In the event that the measured version angle does not correspond to an anticipated/intended value and/or does not fall within an acceptable range of "normal" angles, there are various actions that may be taken.

For instance, in one example, an iterative approach may be taken in which the procedure described herein is repeated a plurality of times as the neck of the femur 100 is being prepared to receive the femoral implant. For instance, while using broaches of different sizes to remove bone from the femoral neck, each broach may be inserted (typically starting with the smallest, thereafter in order of increasing size as more bone is removed) into the medullary canal so that the version angle may be measured using a protractor of the kind described herein. In this way, the surgeon may use the measured version angle as a guide for the subsequent removal of bone from the femur, thereby to attempt to arrive at a finally prepared femur which has an acceptable version angle when the femoral implant is installed.

In another example, the orientation and/or configuration of the acetabular cup implant that may be installed in the acetabulum of the patient as part of the hip replacement procedure may be altered to accommodate the version angle of the restored neck of the femur. In particular, the cup anteversion angle at which the cup implant is installed in the acetabulum may be altered accordingly and/or a different liner may be used in the cup implant.

In a further example, a different femoral implant may be selected for use in the hip replacement procedure. The selected femoral implant may be configured (shaped and dimensioned) such that the version angle of the restored neck of the femur corresponds to an acceptable value. It is envisaged that in order to choose an appropriate implant, broaches 30 of various configurations (e.g. incorporating different degrees of anteversion) may be trialled by inserting them into the medullary canal at the neck of the femur 100 and by using the protractor to measure the version angle. At the end of this process, a femoral implant corresponding to the configuration (e.g. degree of anteversion) of the most appropriate broach may be selected for the prosthetic hip. In a similar approach, a different femoral neck portion may be selected for the femoral implant, to produce a normal amount of anteversion for the implant. Again, the appropriate femoral neck portion may be selected by trialling using different broaches, or a single broach having a connection member for the attachment of different kinds of neck trial portion having different amounts of anteversion.

In another example, an abnormal version angle may be accommodated by adjusting the tension in the soft tissues of the leg (e.g. the abductor muscles, flexors or capsule).

It is envisaged that combinations of the approaches set out above may be used. For instance, in the event that the iterative approach described above does not result in an acceptable version angle, the anteversion angle of the acetabular cup may be altered and/or the tensions in the soft tissues surrounding the hip may be altered.

Accordingly, there has been described an apparatus and method for measuring a version angle of a restored neck of a femur during a hip replacement procedure. The apparatus includes a broach. The broach has a distal end that is insertable into a medullary canal of the neck of the femur. The broach also has a proximal end that extends along a neck axis of the broach. The apparatus also includes a protractor. The protractor includes a rod which is attachable to the proximal end of the broach to extend away from the neck axis of the broach for measuring the version angle of the restored neck of the femur relative to a vertical direction. The method includes inserting the broach, flexing the knee at approximately ninety degrees, orienting the tibia vertically, attaching the protractor to the proximal end of the broach and using it to measure the version angle.

Although particular embodiments of this invention have been described, it will be appreciated that many modifications/additions and/or substitutions may be made within the scope of the claims.

The invention claimed is:

1. Apparatus for measuring a version angle of a restored neck of a femur during a hip replacement procedure, the apparatus comprising:
   a broach comprising a distal end insertable into a medullary canal of the neck of the femur, the distal end having a longitudinal axis and a proximal end extending along a neck axis of the broach, the neck axis being at an angle from the longitudinal axis;
   a protractor comprising a rod which is attachable to the proximal end of the broach to extend away from the neck axis of the broach and generally orthogonal to the longitudinal axis of the broach for measuring the version angle of the restored neck of the femur relative to a vertical direction, wherein the protractor comprises a pendulum pivotably mounted on the rod to hang vertically for measuring the version angle relative to the vertical direction; and
   a stationary marker attached to the rod and separate from the pendulum the for reading off a measurement of the version angle relative to the vertical direction by determining the location of the stationary marker in relation to the orientation of the pendulum, wherein the protractor includes one or more indicia for reading off a measurement of the version angle relative to the vertical direction and the one or more indicia on the protractor are separate from the stationary marker.

2. The apparatus of claim 1, wherein the protractor includes a sleeve portion located on the rod, wherein includes said stationary marker, and wherein the pendulum is pivotably attached to the sleeve portion.

3. The apparatus of claim 1, wherein the protractor includes a bubble level attached to the rod.

4. The apparatus of claim 1, wherein the indicia include a plurality of tick marks for reading off a numerical measurement of the version angle in degrees.

5. The apparatus of claim 1, wherein the indicia include one or more zonal markers for reading off a zonal measurement indicating that the version angle falls within either a normal range, a high range and/or a low range.

6. The apparatus of claim 1, wherein the indicia further include a marker for indicating the vertical direction.

7. The apparatus of claim 1, wherein the protractor includes an electronic inclinometer attached to the rod.

8. The apparatus of claim 1, wherein the rod includes an elongate section set at a predetermined angle relative to the broach, wherein the predetermined angle corresponds to a normal version angle for a patient, for measuring the version angle by judging the orientation of the elongate section relative to the vertical direction.

9. The apparatus of claim 1, wherein the proximal end of the broach comprises a connection member for connecting a neck trial to the broach.

10. The apparatus of claim 9, comprising a neck trial attached to the connection member.

11. The apparatus of claim 9, wherein the rod is attachable to the connection member and/or to the neck trial.

12. The apparatus of claim 1, wherein the proximal end of the broach includes an aperture for receiving the rod, to attach the rod to the proximal end.

* * * * *